(12) United States Patent
Sander

(10) Patent No.: US 7,505,198 B2
(45) Date of Patent: Mar. 17, 2009

(54) MICROSCOPE WITH STAND

(75) Inventor: Ulrich Sander, Rebstein (CH)

(73) Assignee: Leica Microsystems (Schweiz) AG, Heerbrugg (CH)

( * ) Notice: Subject to any disclaimer, the term of this patent is extended or adjusted under 35 U.S.C. 154(b) by 590 days.

(21) Appl. No.: 10/778,689

(22) Filed: Feb. 13, 2004

(65) Prior Publication Data

US 2004/0160667 A1 Aug. 19, 2004

(30) Foreign Application Priority Data

Feb. 15, 2003 (DE) ............................... 103 06 440

(51) Int. Cl.
*G02B 21/32* (2006.01)
(52) U.S. Cl. .................................................. 359/368
(58) Field of Classification Search .................. 359/368
See application file for complete search history.

(56) References Cited

U.S. PATENT DOCUMENTS

| | | | |
|---|---|---|---|
| 3,942,862 A | 3/1976 | Furukawa et al. | |
| 4,970,540 A | 11/1990 | Vasey et al. | |
| 5,101,230 A | 3/1992 | Shikaumi et al. | |
| 5,107,293 A | 4/1992 | Sekine et al. | |
| 5,126,561 A | 6/1992 | Nakazawa et al. | |
| 5,182,671 A | 1/1993 | Kitagishi et al. | |
| 5,243,462 A | 9/1993 | Kobayashi et al. | |
| 5,245,378 A | 9/1993 | Washisu | |
| 5,333,032 A | 7/1994 | Matsumoto et al. | |
| 5,561,498 A | 10/1996 | Sekine et al. | |
| 5,731,896 A | 3/1998 | Baumann et al. | |
| 5,786,936 A | 7/1998 | Baumann et al. | |
| 5,940,630 A | 8/1999 | Washisu | |
| 6,191,813 B1 | 2/2001 | Fujisaki et al. | |
| 6,226,458 B1 | 5/2001 | Kaihara | |
| 6,364,268 B1 * | 4/2002 | Metelski | 248/317 |
| 6,567,212 B1 * | 5/2003 | Engelhardt et al. | 359/368 |
| 2001/0024320 A1 | 9/2001 | Okada | |
| 2003/0016301 A1 | 1/2003 | Aikazi et al. | |

FOREIGN PATENT DOCUMENTS

DE    43 42 538 A1 A    6/1994
DE    43 42 717 A1    6/1994

OTHER PUBLICATIONS

Melcher, J., et al., "Modern Adaptive Real-Time Controllers for Actively Reacting Flexible Structures", Journal of Intelligent Material Systems and Structures, Jul. 1991, vol. 2, pp. 328-346, Technomic Publishing Co., Inc., Lancaster, PA, United States of America.
Breitbach, E.J., et al., "Adaptive Structures—Concepts and Prospects", Institute of Aeroelasticity, Institute of Structural Mechanics, 1993, pp. 1-8, DLR Bibliothek Göttingen, Germany.
Zeiss Information 4 (1995) No. 6, p. 24.

* cited by examiner

*Primary Examiner*—Joshua L Pritchett
(74) *Attorney, Agent, or Firm*—Hodgson Russ LLP

(57) ABSTRACT

The invention concerns a microscope (5) with a stand (1), in which an ARES component (71) is arranged for vibration compensation. A steady subject image is thereby guaranteed in particularly effective fashion.

6 Claims, 2 Drawing Sheets

MICROSCOPE WITH STAND

CROSS REFERENCE TO RELATED APPLICATIONS

This application claims priority of the German patent application 103 06 440.0 which is incorporated by reference herein.

FIELD OF THE INVENTION

The invention concerns a microscope with stand, in particular a surgical microscope.

BACKGROUND OF THE INVENTION

Surgical microscopes are supported by stands that either rest on the floor or are mounted on the wall or ceiling. As a result of utilization of the microscope with its functions such as X/Y displacement, zoom adjustment, and release of the brakes in the articulated arms; or because of external oscillations caused e.g. by the vibrations of passing trucks or insufficiently vibration-isolated air conditioning systems, the microscope can be caused to vibrate, resulting in a visible unsteadiness of the microscope image.

In order to eliminate a visible unsteadiness, there are solutions that are used in photographic lenses and field glasses such as those published e.g. in U.S. Pat. No. 6,226,458 B1, U.S. Pat. No. 6,191,813 B1, U.S. Pat. No. 5,940,630, U.S. Pat. No. 5,561,498, U.S. Pat. No. 5,335,032, U.S. Pat. No. 5,245,378, U.S. Pat. No. 5,243,462, U.S. Pat. No. 5,182,671, U.S. Pat. No. 5,126,561, U.S. Pat. No. 5,107,293, U.S. Pat. No. 5,101,230, U.S. Pat. No. 4,970,540, and U.S. Pat. No. 3,942,862, and in "Zeiss Information" 4 (1995) No. 6, page 24. With these known solutions, the troublesome vibration is sensed either electronically or mechanically, and an optical constituent (e.g. a lens or a prism) is then moved or adjusted in order to compensate for the vibration. This motion or adjustment occurs in regulated fashion, by means of either a motorized drive or mechanical lever forces. U.S. Pat. No. 5,731,896, U.S. Pat. No. 5,786,936, DE-A-43 42 717, and DE-A-43 42 538 also describe comparable systems for surgical microscopes. Here as well, vibrations of the system are measured so as thereby to counter-control an optical element, in this case the main objective.

The description below, especially that of disadvantages, is confined to surgical microscopes, although the invention can also be used successfully with other devices. U.S. Pat. No. 5,731,896, U.S. Pat. No. 5,786,936, DE-A-43 42 717, and DE-A-43 42 538 describe a solution for surgical microscopes in which vibrations of the system are measured. Motors that can move the main objective relative to the microscope in the X/Y plane compensate for this vibration, so that the subject image appears relatively steady in the eyepiece.

An important disadvantage with this known solution occurs because the objective's vibration is compensated for only in the X/Y plane. In the Z direction it continues to vibrate in undamped fashion. Vibrations that can no longer be compensated for by the depth of focus of the objective therefore have a severe impact on the contrast and sharpness of the subject image.

A further disadvantage is also that the entire microscope can continue to vibrate relative to the observing surgeon; in some circumstances, as a result of excessive vibration he or she can lose the exit pupil or be presented with a vignetted image.

In order to eliminate the latter disadvantage, an obvious choice is to compensate for vibrations of the entire optical system. Such solutions have been proposed, for example in U.S. Pat. No. 5,731,896, U.S. Pat. No. 5,786,936, DE-A-43 42 717, and DE-A-43 42 538.

Here motors move the entire microscope in the X/Y plane in order to compensate for vibrations, so that the subject image appears relatively steady in the eyepiece. Here again, however, no compensation is performed in the Z direction, and it is disadvantageous that the motors must move greater masses.

SUMMARY OF THE INVENTION

It is thus the object of the invention to discover a lightweight and compact vibration compensation device for the entire optical system which compensates for vibrations not only in the X and Y axes but also in the Z axis, i.e. three-dimensionally. This object is achieved by an apparatus comprising a microscope having a main objective and a stand for supporting the microscope, wherein at least one of the stand and the microscope includes an actively reacting flexible structure (ARES) component arranged to compensate vibrations.

BRIEF DESCRIPTION OF THE DRAWINGS

The Figures are described in interconnected and overlapping fashion. Identical reference characters denote identical components; reference characters having different indices indicate functionally identical components. In the drawings.

DETAILED DESCRIPTION OF THE INVENTION

Figure 1:
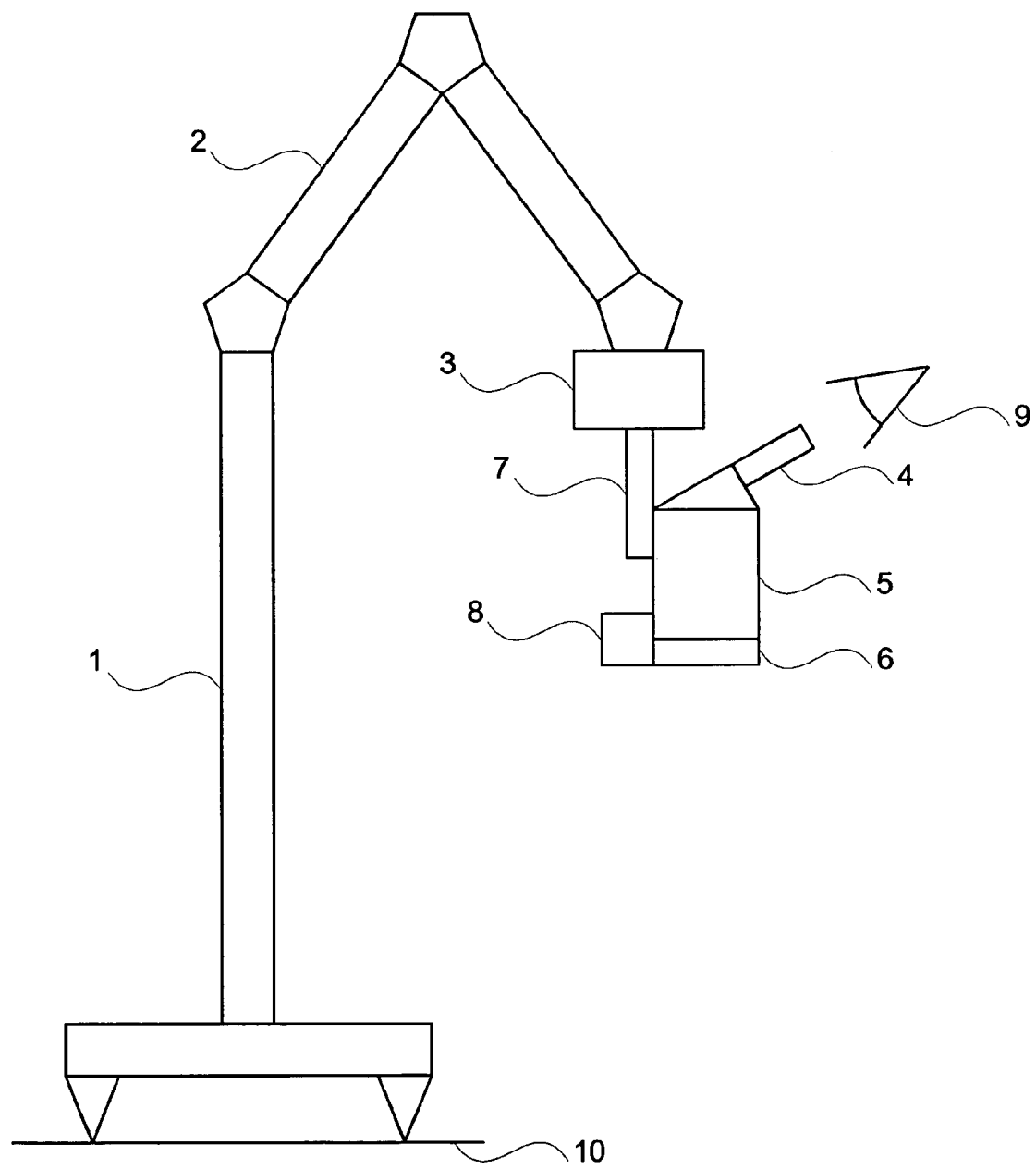
FIG. 1 is a side view of a known surgical microscope.

FIG. 1 depicts a surgical microscope 5 with stand 1 according to the existing art, standing on floor 10. Stand 1 has a movable pantograph arm 2 for unrestricted positioning in space, at whose free end is arranged an X/Y adjustment system 3 for controlled precision orientation by the observer. Microscope 5, including main objective 6 and a tube with eyepiece 4 for user's eye 9, is mounted here by means of a support arm 7.

A motor with sensors 8 for vibration compensation is located directly in the region of main objective 6, where it acts on the later as adjusting element. Motor with sensors 8 can also, according to the existing art, be mounted between pantograph arm 2 and support arm 7, or between support arm 7 and microscope 5 (not depicted in FIG. 1).

Figures 2, 3:
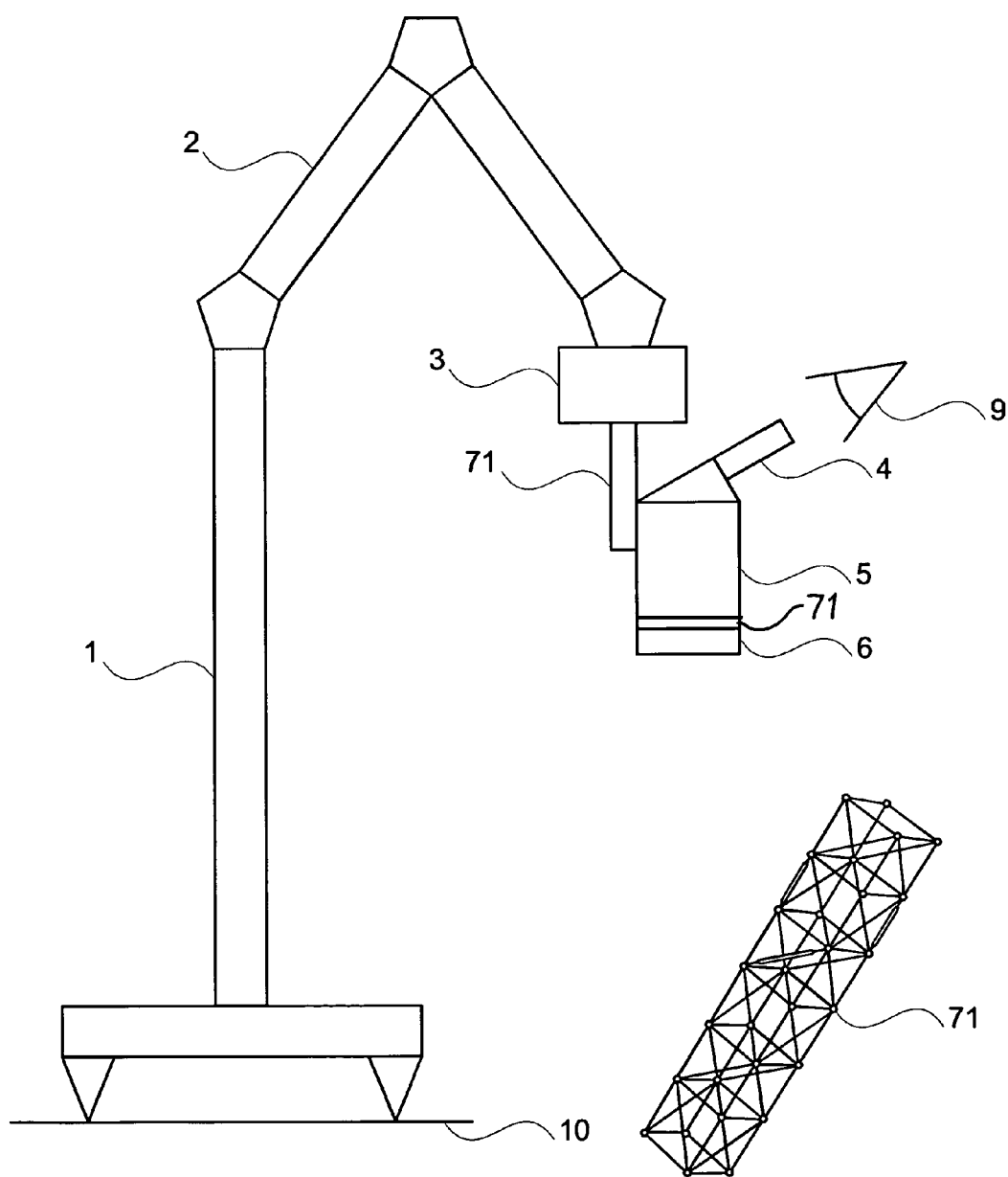
FIG. 2 is a side view of a surgical microscope with stand according to the present invention.
FIG. 3 is a perspective depiction of an ARES component.

FIG. 2 depicts a surgical microscope 5 with stand 1 according to the present invention, standing on floor 10. Stand 1 has a movable pantograph arm 2 for unrestricted positioning in space, at whose end is arranged an X/Y adjustment system 3 for controlled precision orientation by the observer. Here, however, an ARES component 71 which carries microscope 5 including main objective 6 and tube with eyepiece 4 is provided in place of support arm 7 as shown in FIG. 1. Another ARES component 71 is arranged inside microscope 5 to support main objective 6.

ARES components are described in the article by E. J. Breitbach et al., "Adaptive Structures—Concepts and Prospects" of the Institute of Aeroelasticity and the Institute of Structural Mechanics of the German Aerospace Research Establishment (DLR), pages 3-8 (publication date unknown).

An ARES component is a self-regulating component that, on the basis of a measurement of vibrations, activates integrated drive elements in such a way that they counteract the vibration in real time so that the vibration does not result in a positional change in the external contours or critical interfaces of the constituent part. Acceleration sensors in or in the vicinity of the ARES component itself measure those vibrations and compensate for them directly by way of a variation of the ARES component in the XYZ directions, so that according to the present invention, the entire microscope is steady in all three dimensions relative to the observer or relative to the room.

A further advantage of the invention is constituted by a reduction in the number of constituent parts, provided the ARES components directly replace the support arm, i.e. serve simultaneously as a supporting element and not only as a vibration-compensating element. Bulky and heavy motors with sensors in the region of the microscope, or additional optical compensation elements, are thus eliminated, together with the visual impediments resulting therefrom. For purposes of the disclosure of this Application, reference is made to the content of the aforementioned article by Breitbach et al., which is incorporated herein by reference.

An ever-ncreasing number of candidate materials and material systems for adaptive structure sensors and actuators exist, for example:

Piezopolymers, e.g. PVDF
Piezoceramics, e.g. PZT
Electrostrictive ceramics
Magnetostrictive rare earth alloys
Shape memory alloys, e.g. NiTi
Shape memory polymers
Electro-theological fluids
Magneto-rheological fluids
Glass fiber sensors
Magnetic fluids
Bi-metal combinations, In order to be able to effectively design, evaluate, and select adaptive structures before their construction, in any particular application it is necessary to precisely understand their static and dynamic mechanical behavior. For this purpose, methods for the analysis and optimization of adaptive structures must be developed. The main technical objectives for the design of adaptive structures are outlined as follows:

The development of constitutive equations of available materials and their implementation into software codes, e.g. finite element codes. It is emphasized that the constitutive equations of all the smart materials under consideration have to take into account coupling effects, for example, a thermo-mechanical coupling in the case of shape memory alloys.

Based on the above-mentioned constitutive equations, the development of mathematical models of multifunctional actuators and sensors, e.g. finite elements for plates and shells with piezo-electric polymers bonded to the surface or beam and truss elements for composite structures with embedded shape memory alloy wires. These advanced finite elements are necessary, for instance, for the discretization of the space structure shown on the cover. The finite shell elements are used for the active parts of the antenna structure, the truss elements for the multifunctional struts.

The development of algorithms that describe multifunctional components in order to optimize smart structures with regard to sensor and actuator positions. Typically, the optimization algorithm must produce the best structural configuration, balancing the conflicting aspects of different objectives.

The integration of the control concept into the mathematical model to allow precise evaluation of adaptive structures.

Recent developments of high-speed processors have made it possible to ran controllers under real-time conditions, resulting in a decisive step towards the breakthrough of adaptive structures.

The main goals for controllers in adaptive structures applications are to process the signals from the multifunctional sensors and
generate the optimal driving signals for the multifunctional actuators.

Adaptive structures are systems that may vary with time in the face of changing nonstationary environments or system requirements. In situations where structural system parameters are variable or not accurately known, adaptive or self-optimizing controllers must be used. These controllers are able to adapt their behavior and performance to their environment according to the desired criterion.

Adaptive control systems based on advanced concepts of digital signal processing are considered the best possible means to solve the control requirements of adaptive structures.

Such controllers consist of different digital filter systems combined with corresponding adaptation algorithms. The property of structural conformity can be achieved by considering an a priori knowledge of the structure when choosing the controller filter type. This development step is quite similar to that of the new on-line system identification method use adaptive MX filters.

By using such control concepts, the knowledge of the optimized actuator and sensor locations from the finite element analysis can be effectively considered.

A typical adaptive space structures approach is illustrated on the cover page—a generic truss structure. Such systems are generally affected by static distortions and transient vibrations. Both effects can be compensated by using built-in active multifunctional struts, keeping the supported load (microscope 5) in the correct position.

Further embodiments of the invention are described in FIGS. 2 and 3 and in the dependent claims.

The microscope or stand uses for vibration compensation one ARES component preferably at a potential point of occurrence of vibration antinodes, or several ARES components at different points.

An ARES component can be arranged either as a supporting element itself in place of a supporting element in order to decouple the microscope vibrationally from the rest of the stand, i.e. between the stand and microscope; or inside the microscope for direct decoupling of the main objective. The ARES component can be activated not only for vibration compensation, but also nonvibrationally for positional stabilization. An ARES component can be powered piezoelectrically and can thus function, if applicable, independently of ordinary electrical circuits. In this context, piezoelectric crystals are stimulated by the geometrical change to generate voltage, that voltage being used to stimulate other piezoactuators for counter-control. These embodiments can also refer to surgical microscopes or surgical stereomicroscopes.

The invention will be explained further, in symbolic and exemplary fashion, with reference to schematic Figures.

FIG. 3 depicts an example of an ARES component 71, which has a three-dimensional truss structure and, in the context of the microscope according to the present invention, replaces (and thus makes superfluous) support arm 7 as well as the functionality of motor with sensors 8 of the microscope described in FIG. 1.

PARTS LIST

1 Stand
2 Pantograph arm (supporting part)
3 X/Y adjustment system
4 Tube with eyepiece 4
5 (Surgical) microscope
6 Main objective
7 Support arm (supporting part)
8 Motor with sensors
9 Observer's eye(s)
10 Floor
71 ARES component

What is claimed is:

1. An apparatus comprising:
   a stand including a supporting part; and
   a microscope mounted as a unit on the stand, the microscope having a main objective, a tube, and an eyepiece; wherein the supporting part of the stand is an Actively Reacting Flexible Structure (ARES) component formed as a three-dimensional truss, the ARES component actively compensating vibrations of the microscope as a whole along X, Y, and Z directions.

2. The apparatus as defined in claim 1, wherein the ARES component supporting part is arranged between the microscope and the rest of the stand in order to decouple the microscope from the rest of the stand.

3. The apparatus as defined in claim 1, wherein the ARES component supporting part includes a piezoelectric energy supply system.

4. The apparatus as defined in claim 1, wherein the ARES component supporting part is activated not only for vibration compensation, but also nonvibrationally for positional stabilization.

5. The apparatus as defined in claim 1, wherein the microscope is a surgical microscope.

6. The apparatus as defined in claim 5, wherein the surgical microscope is a surgical stereomicroscope.

* * * * *